United States Patent [19]

Baldi et al.

[11] 4,328,369

[45] May 4, 1982

[54] PROCESS FOR THE PRODUCTION OF 2,6-DINITRO-N-ALKYL-ANILINES

[75] Inventors: Luciano Baldi, Turin; Franco Collecchia, Borgaro; Vittorio Messori, Turin, all of Italy

[73] Assignee: Rumianca S.p.A., Turin, Italy

[21] Appl. No.: 224,998

[22] Filed: Jan. 14, 1981

[51] Int. Cl.$^3$ .............................................. C07C 85/04
[52] U.S. Cl. ..................................... 564/406; 564/437
[58] Field of Search ................................ 564/406, 407

[56] References Cited

U.S. PATENT DOCUMENTS 1,401,631 12/1921 Moran ................................ 564/406

FOREIGN PATENT DOCUMENTS 2161879 6/1973 Fed. Rep. of Germany ...... 564/406

*Primary Examiner*—John Doll
*Attorney, Agent, or Firm*—Sughrue, Mion, Zinn, Macpeak and Seas

[57] ABSTRACT

2,6-dinitro-N-alkyl-anilines are prepared by continuously delivering a 2,6-dinitro-chlorobenzene, a dialkylamine, an inorganic base and water to a tubular reaction zone and operating in said reaction zone under turbulent conditions, at a temperature not exceeding 150° C., for a short reaction time and with substantially complete conversion of the chlorobenzene.

13 Claims, No Drawings

PROCESS FOR THE PRODUCTION OF 2,6-DINITRO-N-ALKYL-ANILINES

BACKGROUND AND SUMMARY OF THE INVENTION

The present invention relates to an improved process for the continuous preparation of 2,6-dinitro-N-alkyl-anilines of the general formula (1):

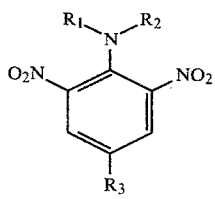

in which $R_1$ and $R_2$ represent independently a saturated or unsaturated hydrocarbon radical containing from 1 to 6 atoms of carbon, or a cycloalkyl radical containing from 3 to 6 atoms of carbon in the ring, and in which $R_3$ represents an atom of hydrogen, an alkyl radical containing from 1 to 4 atoms of carbon, or an alkyl radical with from 1 to 4 atoms of carbon in which the hydrogen atoms are partially or completely substituted by halogen atoms.

Among the 2,6-dinitro-N-alkyl-anilines represented by the general formula (1) are numerous herbicides and, among these, the best known are: 2,6-dinitro-4-isopropyl-N,N-dipropyl-aniline (Isopropalin); 2,6-dinitro-4-trifluoromethyl-N,N-dipropylaniline (Trifluralin); 2,6-dinitro-4-trifluoromethyl-N-cyclopropylmethyl-N-propyl-aniline (Profluralin); and 2,6-dinitro-4-trifluoromethyl-N-butyl-N-ethyl-aniline (Benfluralin). The herbicidal characteristics of these compounds and of other similar compounds are described in U.S. Pat. Nos. 3,257,190 and 3,403,180.

In particular the compounds corresponding to the general formula (1) in which $R_3$ is a trifluoromethyl group are generally prepared from 2,6-dinitro-4-trifluoromethyl-chlorobenzene by substitution of the chlorine atom by reaction with an amine $NHR_1R_2$, in which $R_1$ and $R_2$ have the meaning already indicated above.

In practice, the reaction is carried out according to the general scheme:

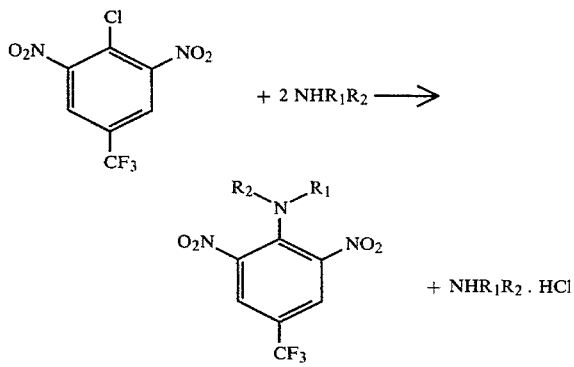

by reacting 2,6-dinitro-4-trifluoromethyl-chlorobenzene with two equivalents of the amine (which thus also acts as the acceptor for the hydrochloric acid which is formed as a by-product of the reaction) in a discontinuous operation, to obtain the desired 2,6-dinitro-4-trifluoromethyl-N-alkyl-aniline.

In the literature, and particularly in patent literature, other processes are described for the preparation of 2,6-dinitro-N-alkyl-anilines represented by the general formula (1).

Thus, for example, according to U.S. Pat. No. 3,403,180, 2,6-dinitro-chlorobenzene, possibly substituted in the 4-position of the benzene ring, and two equivalents of the chosen amine are reacted by heating the reaction mixture for a time of 2 to 4 hours. This method is disadvantageous in that the use of the amine as the acceptor for hydrochloric acid makes necessary the separation of the hydrochloride of the amine from the reaction mixture and the subsequent treatment of the said hydrochloride with an alkali metal hydroxide (generally sodium hydroxide) to recover the said amine. In French Pat. No. 2,051,301, an attempt was made to avoid the disadvantages resulting from the presence of the amine as the acceptor for hydrochloric acid by using a mineral base, such as sodium hydroxide or sodium carbonate, for this purpose. According to the process described in this French Patent, the 2,6-dinitro-chlorobenzene is fed into a dilute solution of sodium hydroxide (about 8% concentration) and the amine is gradually added to the suspension obtained, the reaction temperature being maintained at values less than about 15° to 20° C. by cooling the reaction mass. After this addition, which requires a time of the order of three hours, the mass is heated to 80° C. and left to react for a further two hours. This method also has numerous disadvantages. First of all, the total reaction time is of the order of 5 hours and, furthermore, there are the complexities resulting from the cooling and the subsequent heating of the reaction mass. Moreover, since the reaction is carried out in a two-phase system, very strong agitation is necessary in order to achieve satisfactory contact between the aqueous alkaline phase and the organic phase. Finally, the low concentration of sodium hydroxide in its solution, dictated by the need to reduce the side reactions, necessitates the use of large reaction volumes and hence results in a low productive capacity, this being understood as the quantity of desired product per unit of useful volume of the reactor. It should also be noted that the conversion into the desired product is of the order of 91–93% according to the patent under discussion.

This shows that, under the reaction conditions used, an amount of 2,6-dinitro-chlorobenzene of the order of 7 to 9% is lost owing to side reactions, which, on the one hand, renders the process hardly economic, and, on the other hand, aggravates the problems resulting from the disposal of the aqueous effluent.

Hence the known art does not allow 2,6-dinitro-N-alkyl-anilines to be produced with high values of the yield and selectivity.

Moreover, the known art does not teach any method of achieving high values of the yield and selectivity in a reaction system which is simple and easy to operate in a continuous manner.

With this in mind, it should be remembered that a continuous system has potentially, with respect to discontinuous processes, the capacity for providing a greater yield in a given time per unit useful volume of the reactor, a greater possibility of automating the plant and better constancy in the characteristics of the product obtained. The difficulties explained above have, until now, prevented the realisation of advantageous processes for the continuous production of 2,6-dinitro-N-alkyl-anilines.

The object of the present invention is to overcome the disadvantages of the known art relating to the preparation of 2,6-dinitro-N-alkyl-anilines.

DETAILED DESCRIPTION OF THE INVENTION

The present invention is based essentially on the finding that the reaction of 2,6-dinitro-chlorobenzene, with or without a substituent in the 4-position, with an amine occurs at a high speed, substantially up to completion and with negligible formation of undesirable by-products, in a tubular reaction zone in which the reagent mass is maintained under turbulent conditions and at a relatively high temperature.

Accordingly, the invention provides a continuous process for the preparation of 2,6-dinitro-N-alkyl-aniline of the formula:

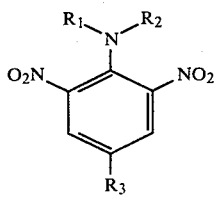

(I)

wherein $R_1$ and $R_2$ independently are a saturated or unsaturated hydrocarbon radical with from 1 to 6 carbon atoms, or a cycloalkyl radical with from 3 to 6 carbon atoms in the ring, and $R_3$ is hydrogen, an alkyl radical with from 1 to 4 carbon atoms or an alkyl radical with from 1 to 4 carbon atoms in which the hydrogen atoms are partially or completely substituted by halogen atoms, by reacting a 2,6-dinitro-chlorobenzene of the formula:

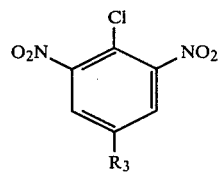

(II)

with an amine $NHR_1R_2$, wherein $R_3$, $R_1$ and $R_2$ have the same meaning as in formula (I), characterized by continuously feeding said chlorobenzene (II) to the inlet end of a tubular reaction zone, continuously feeding an inorganic base, said amine and water to said tubular reaction zone, said inorganic base and said amine being fed in at least in part to the inlet end of said tubular reaction zone, said chlorobenzene, inorganic base and amine being fed in in substantially stoichiometric proportions and reacted in said tubular reaction zone in the liquid phase, under turbulent conditions and at a temperature not exceeding 150° C. to convert substantially completely said chlorobenzene (II) into said aniline (I), continuously discharging the resulting reaction products from the outlet end of said tubular reaction zone and recovering said aniline (I) from said reaction products.

Preferably, the equivalent ratio between chlorobenzene (II), amine and inorganic base fed in is from 1:1:1 to 1:1.1:1.3. Conveniently, a slight excess of inorganic base with respect to the chlorobenzene is maintained in the feed, for example an equivalent excess of the order of 5–15%. The amine is generally fed in wholly to the inlet end of the tubular reaction zone, and the inorganic base may be fed in wholly or in part to the inlet end of said zone.

The inorganic base is generally fed in in the form of an aqueous solution, having for example a concentration of from 10 to 30%, and preferably from 15 to 25% by weight. The inorganic base is preferably chosen from alkali metal hydroxides and carbonates, best results being generally obtained with sodium hydroxide.

The amine is generally fed in in the form of an aqueous solution, which may also contain the inorganic base. In the case in which the amine is insoluble or scarcely soluble in water, an independent feed for the said amine may be provided. Examples of suitable amines are di-propylamine, propyl-cyclopropylmethylamine, dibutyl-amine, di-isopropylamine, ethyl-propylamine and ethyl-hexylamine.

The chlorobenzene (II) may be fed in in the liquid form or in the form of a solution in an organic solvent inert (non-reactive) under the reaction conditions and having a good solvating power for the desired aniline (I). Examples of chlorobenzenes are those represented by formula (I) in which $R_3$ is hydrogen, or a methyl, ethyl, propyl, isopropyl, butyl, sec-butyl, tert-butyl, isobutyl or trifluoromethyl radical. In general, when using a mixture of water and organic solvent as the reaction medium, the water/solvent weight ratio is conveniently maintained at a value of from 0.5:1 to 5:1 and preferably from 0.4:1 to 1:1.

Examples of suitable solvents are ethers and cyclic ethers, such as dioxan; ketones, such as acetone and methyl ethyl ketone; aromatic hydrocarbons, such as benzene, toluene and xylene; halogenated aromatic hydrocarbons, such as chlorobenzene; halogenated aliphatic hydrocarbons, such as carbon tetrachloride; and light naphthas. These solvents may be used mixed with water both in the form of single phase systems, such as water-dioxan, and in the form of two-phase systems, such as water-xylene and water-carbon tetrachloride.

The reaction temperature may vary within a range of values of from ambient temperatures (18° to 25° C.) up to a maximum of about 150° C. More particularly, it is possible to carry out the reaction under isothermal, or essentially isothermal, conditions with heat exchange such as to maintain the temperature at a value preferably within the range 40° C. to 100° C. Preferably, the reaction is carried out under adiabatic conditions with a maximum temperature not greater than about 150° C. By adiabatic conditions it is intended, either that there should be no heat exchange at all, whereby the temperature would rise from the value at the inlet to the reactor up to a maximum value which depends on the degree of exothermicity of the reaction, or that this temperature increase should be controlled by means of heat exchange conditions which differ in the various zones along the reactor.

When the reaction is carried out under adiabatic conditions the temperature of the reagents at the inlet is not critical in that the reaction starts easily, even at relatively low temperatures, and the temperature subsequently increases due to the exothermic nature of the reaction.

Reactors useful for carrying out the reaction are elongate tubular reactors having a high length/diameter ratio, for example greater than 2:1, preferably greater than 100:1. Further, according to a basic aspect of the present invention, turbulent conditions are maintained in the reaction mass within the reactor and this may be effected by a suitable choice of the diameter of the reactor and of the linear velocity of the reagent mass, or by means of the use of agitators, or by the introduction into the reactor of filling bodies (of spherical, helical or other form), of partial diaphragms, foraminous plates and the like. In general the reaction is made to proceed very well with a turbulence of the reagent mass, expressed as a Reynold number, greater than about 2500. This may be achieved by making use of several of the factors described above. Thus, for example, in a tubular reactor with a diameter of the order of 2-3 cms, provided with filling bodies, a linear velocity greater than about 0.5 meters/second is conveniently maintained in the case of a single-phase system. In the case of a two-phase system, it is convenient to ensure that the dimensions of the disperse phase are less than 100 microns, and preferably less than 10 microns. To this end one may resort to the addition of surface active agents which may conveniently be fed to the reaction medium together with the reagents.

The reaction in the tubular reactor is preferably brought to completion, or substantial completion, in a time of from a few seconds to a few minutes (typically from 0.5 to 2 minutes) and, in every case, in less than 10 minutes.

By operating under the conditions indicated above, the 2,6-dinitro-N-alkyl-aniline compounds defined by the general formula (1) are obtained with a purity of 99% or more, which shows the great selectivity of the reaction for the desired useful products. Finally, the reaction yields are pratically stoichiometric in that pratically total conversion of the reagents occurs.

In view of these results, it is held that, by carrying out the reaction at relatively high temperature and hence with a high reaction kinetics in a fluodynamic system such as that of the present invention, the formation of the desired reaction product is promoted. This is contrary to the teaching of the known art whereby the amount of undesirable by-products is reduced either by using an amine to block the halogen hydracid which is formed in the reaction or, when an inorganic base is used as the acid acceptor, by operating at low temperatures (particularly in the first reaction stage) and for a total reaction period of the order of 2-5 hours.

The reaction products discharged at the outlet end of the reactor are subjected to the usual treatments for separating the 2,6-dinitro-N-alkyl-aniline.

Thus, for example, the reaction mixture may be conveyed to a phase separator from which the desired product may be recovered in the form of a solution, or in the molten state. According to another embodiment the reaction mixture is conveyed, without cooling, to apparatus for the distillation and recovery of the solvent. The distillation residue is then treated to recover the useful product.

EXAMPLE

Preparation of
2,6-dinitro-4-trifluoromethyl-N,N-dipropyl-aniline

A reactor consisting of a stainless steel tube having a length of 4150 mm, an internal diameter of 4 mm and an external diameter of 6 mm is used. The tube is filled with sand grains having a size of 1.2 to 1.8 mm, an apparent density of 1.48 g/ml and a relative density of 2.6 g/ml.

To the inlet to the reactor are fed independently, by means of metering pumps, a 48.2% by weight solution of 2,6-dinitro-4-trifluoromethyl-chlorobenzene in xylene, at a rate of 21 ml/minute; an aqueous 21.5% by weight sodium hydroxide solution at a rate of 6.5 ml/minute and 99% dipropylamine at a rate of 7 ml/minute. Thus the molar ratio between 2,6-dinitro-4-trifluoromethyl-chlorobenzene and dipropylamine is 1:1.05.

The reaction is carried out under adiabatic conditions with a temperature of the reagents at the inlet equal to ambient values (18°-20° C.) and with a temperature of the mixture about 2 meters from the start of the reactor of 60°-70° C.

The mixture leaving the reactor is acidified with 1 N sulphuric acid and is conveyed to a hot phase separator. The aqueous phase is discharged and, after removal of the solvent from the organic phase by distillation, the 2,6-dinitro-4-trifluoromethyl-N,N-dipropylaniline is recovered with a purity of at least 99%. The yield calculated on the 2,6-dinitro-4-trifluoromethyl-chlorobenzene fed in is 99%.

We claim:
1. A continuous process for the preparation of 2,6-dinitro-N-alkyl-aniline of the formula:

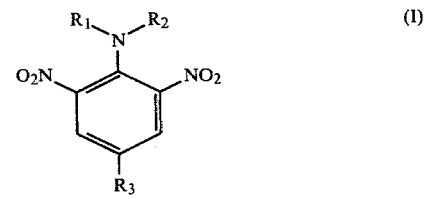

wherein $R_1$ and $R_2$ independently are a saturated or unsaturated hydrocarbon radical with from 1 to 6 carbon atoms, or a cycloalkyl radical with from 3 to 6 carbon atoms in the ring, and $R_3$ is hydrogen, an alkyl radical with from 1 to 4 carbon atoms or an alkyl radical with from 1 to 4 carbon atoms in which the hydrogen atoms are partially or completely substituted by halogen atoms, by reacting a 2,6-dinitro-chlorobenzene of the formula:

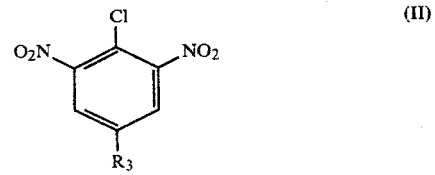

with an amine $NHR_1R_2$, wherein $R_3$, $R_1$ and $R_2$ have the same meaning as in formula (I), which comprises continuously feeding said chlorobenzene (II) to the inlet end of a tubular reaction zone, continuously feeding an inorganic base, said amine and water to said tubular reaction zone, said inorganic base and said amine being fed in at least in part to the inlet end of said tubular reaction zone, said chlorobenzene, inorganic base and amine being fed in in substantially stoichiometric proportions and reacted in said tubular reaction zone in the liquid phase, under turbulent conditions and at a temperature not exceeding 150° C. to convert substantially completely said chlorobenzene (II) into said aniline (I), continuously discharging the resulting reaction products from the outlet end of said tubular reaction zone and recovering said aniline (I) from said reaction products.

2. The process of claim 1, wherein the equivalent ratio between chlorobenzene (I), amine (II) and inorganic base is from 1:1:1 to 1:1.1:1.3.

3. The process of claim 1, wherein said amine (II) is fed in wholly to the inlet end of said tubular reaction zone.

4. The process of claim 1 or 3, wherein said inorganic base is fed in wholly to the inlet end of said tubular reaction zone.

5. The process of claim 1, wherein said inorganic base is chosen from alkali metal hydroxides and carbonates.

6. The process of claim 1, wherein said inorganic base is sodium hydroxide.

7. The process of claim 1, wherein the reaction is carried out under isothermal conditions at a temperature of from 40° to 100° C.

8. The process of claim 1, wherein the reaction is carried out under adiabatic conditions.

9. The process of claim 1, wherein the reaction time in said tubular reaction zone is less than 10 minutes.

10. The process of claim 9, wherein said reaction time is from 0.5 to 2 minutes.

11. The process of claim 1, wherein said chlorobenzene (II) is fed into the tubular reaction zone in the form of a solution in an organic solvent inert under the reaction conditions.

12. The process of claim 1, wherein said tubular reaction zone has a length/diameter ratio greater than about 100:1.

13. The process of claim 1, wherein the turbulence of the reaction medium, expressed as a Reynold number, is greater than about 2500.

* * * * *